US008284986B2

(12) United States Patent
Wolowelsky et al.

(10) Patent No.: US 8,284,986 B2
(45) Date of Patent: Oct. 9, 2012

(54) METHOD FOR REMOTE SPECTRAL ANALYSIS OF GAS PLUMES

(75) Inventors: Karni Wolowelsky, Misgav (IL); Zvi Figov, Beit Shemesh (IL)

(73) Assignee: Rafael Advanced Defense Systems Ltd, Haifa (IL)

( * ) Notice: Subject to any disclaimer, the term of this patent is extended or adjusted under 35 U.S.C. 154(b) by 860 days.

(21) Appl. No.: 12/416,981

(22) Filed: Apr. 2, 2009

(65) Prior Publication Data
US 2009/0257622 A1    Oct. 15, 2009

(30) Foreign Application Priority Data

Apr. 9, 2008    (IL) ............................................ 190757

(51) Int. Cl.
*G06K 9/00*    (2006.01)
*G01N 7/00*    (2006.01)
(52) U.S. Cl. .......................... 382/100; 382/294; 73/23.2
(58) Field of Classification Search .................. 382/100, 382/154, 191, 207, 294; 73/23.2; 250/339.13
See application file for complete search history.

(56) References Cited

U.S. PATENT DOCUMENTS

| 3,931,462 | A | * | 1/1976 | Exton | 348/162 |
| 4,320,975 | A | * | 3/1982 | Lilienfeld | 356/364 |
| 4,434,368 | A | * | 2/1984 | Liesch et al. | 250/339.14 |
| 5,319,199 | A | * | 6/1994 | Stedman et al. | 250/338.5 |
| 5,468,964 | A | * | 11/1995 | Gopalsami et al. | 250/393 |
| 6,295,859 | B1 | * | 10/2001 | Hayden et al. | 73/23.2 |

* cited by examiner

*Primary Examiner* — John Strege
(74) *Attorney, Agent, or Firm* — Mark M Friedman (57) ABSTRACT

A method for reducing the effects of background radiation introduced into gaseous plume spectral data obtained by an aerial imaging sensor, includes capturing spectral data of a gaseous plume with its obscured background along a first line of observation and capturing a second image of the previously obscured background along a different line of observation. The parallax shift of the plume enables the visual access needed to capture the radiometric data emanating exclusively from the background. The images are then corresponded on a pixel-by-pixel basis to produce a mapping. An image-processing algorithm is applied to the mapped images to reducing the effects of background radiation and derive information about the content of the plume.

5 Claims, 10 Drawing Sheets

METHOD FOR REMOTE SPECTRAL ANALYSIS OF GAS PLUMES

FIELD AND BACKGROUND OF THE INVENTION

The present invention relates to remote sensing of gaseous materials through multi-spectral analysis via satellite, aerial, or ground based platforms and, in particular, it is concerned about reducing the effects of background radiation introduced into the spectral data.

Figure 1:
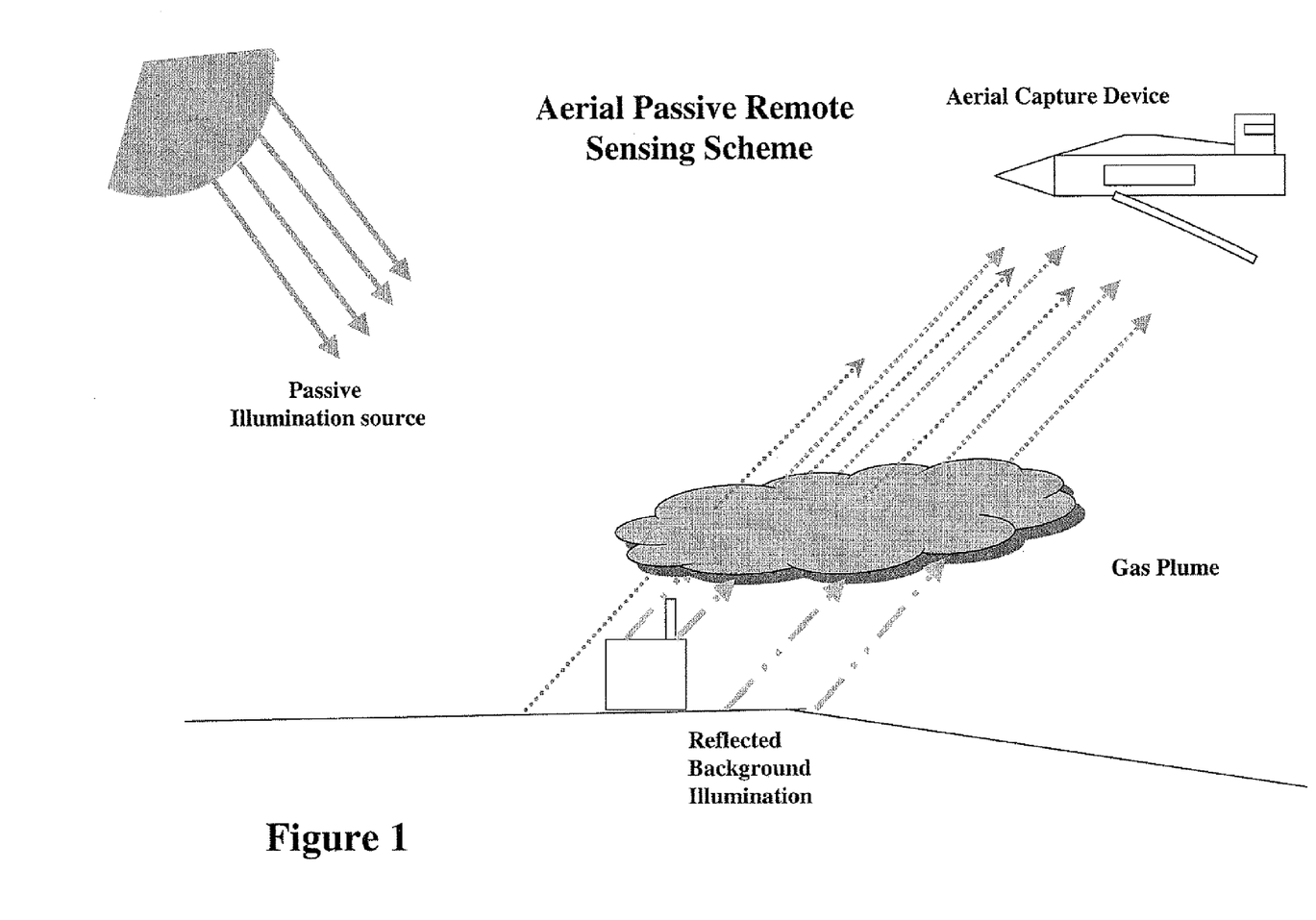
FIG. 1 depicts an aerial, passive remote sensing scheme.
Figure 2:
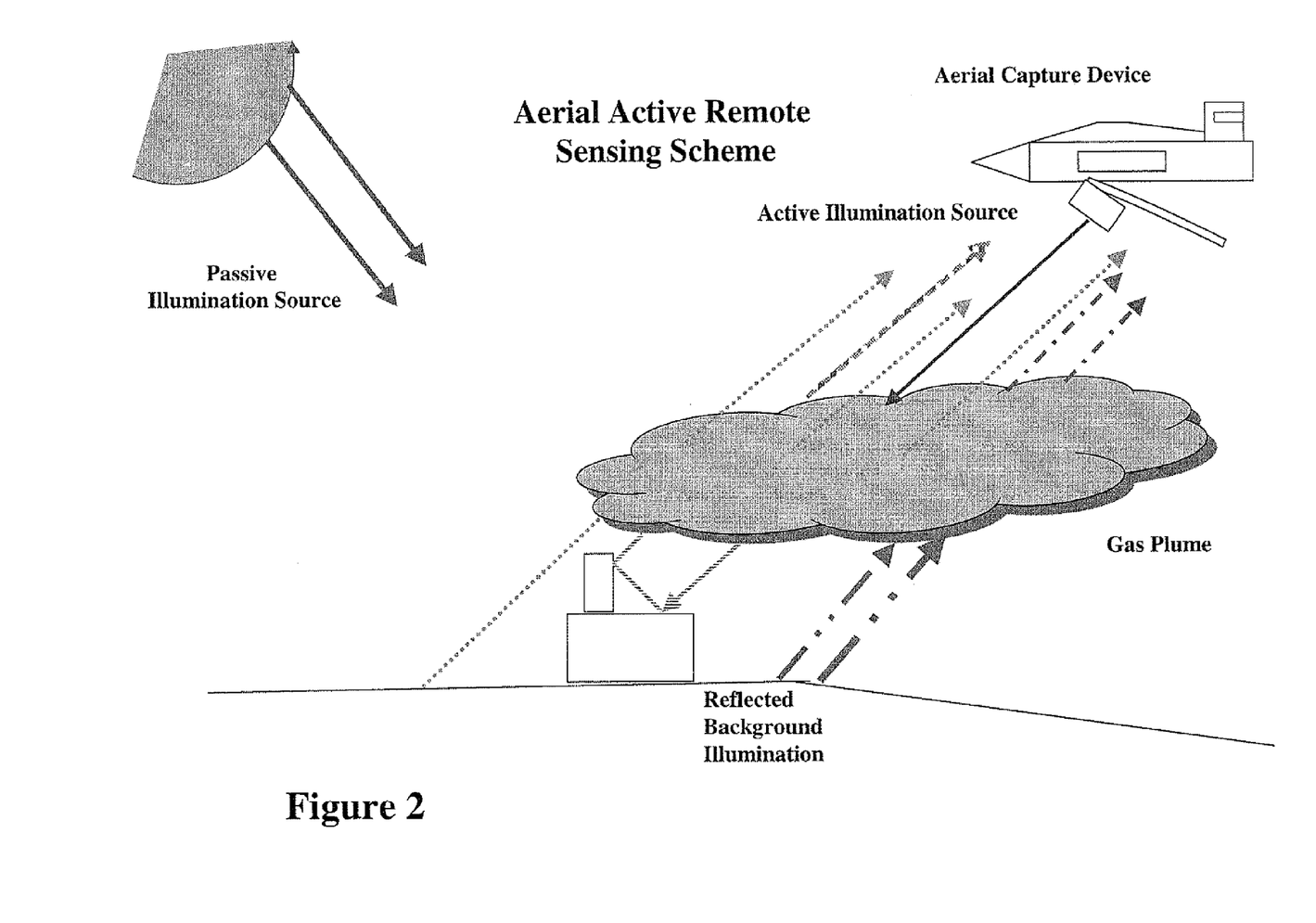
FIG. 2 depicts an aerial, active remote sensing scheme.
Figure 3:
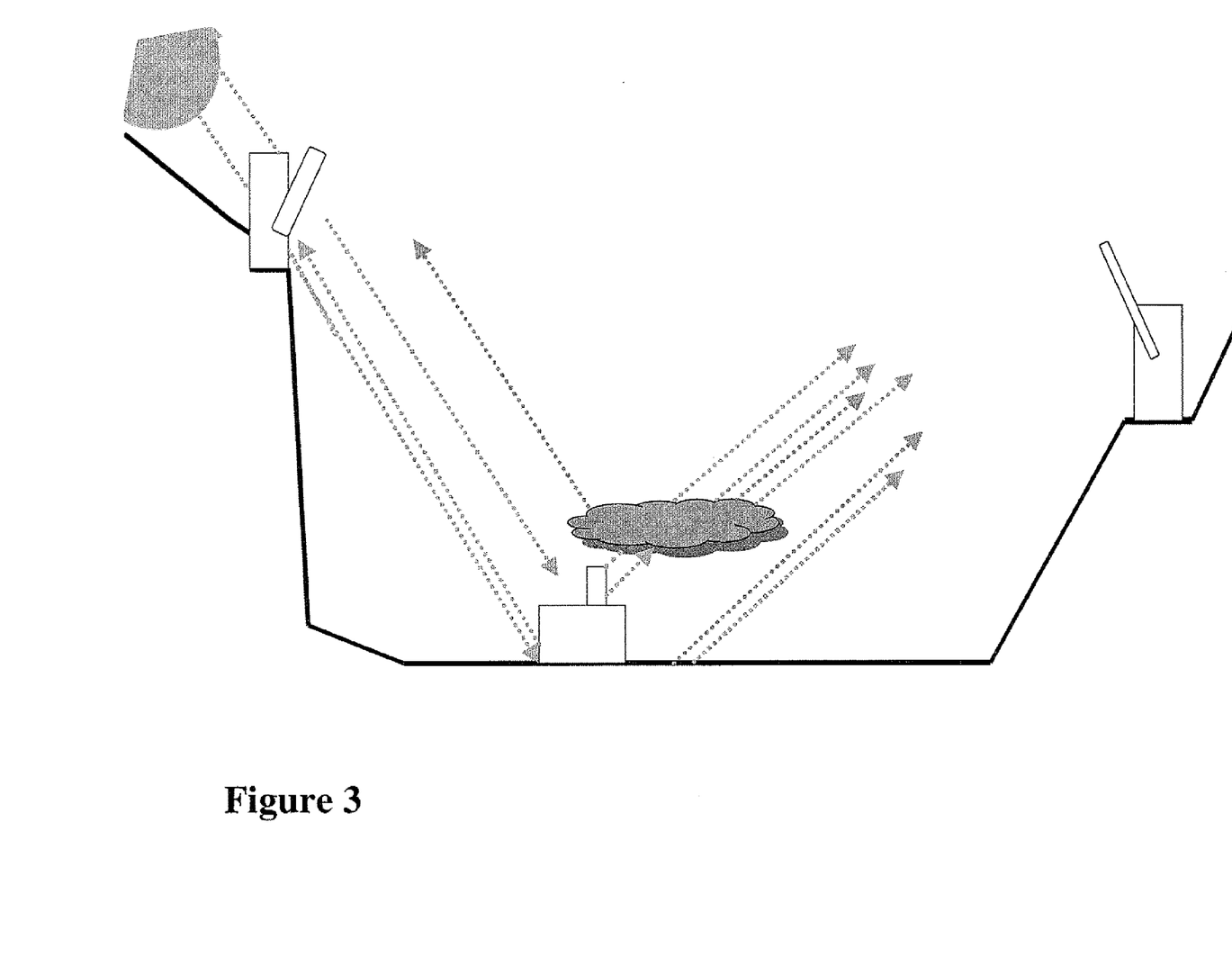
FIG. 3 depicts a ground-based passive remote sensing scheme.
Figure 4:
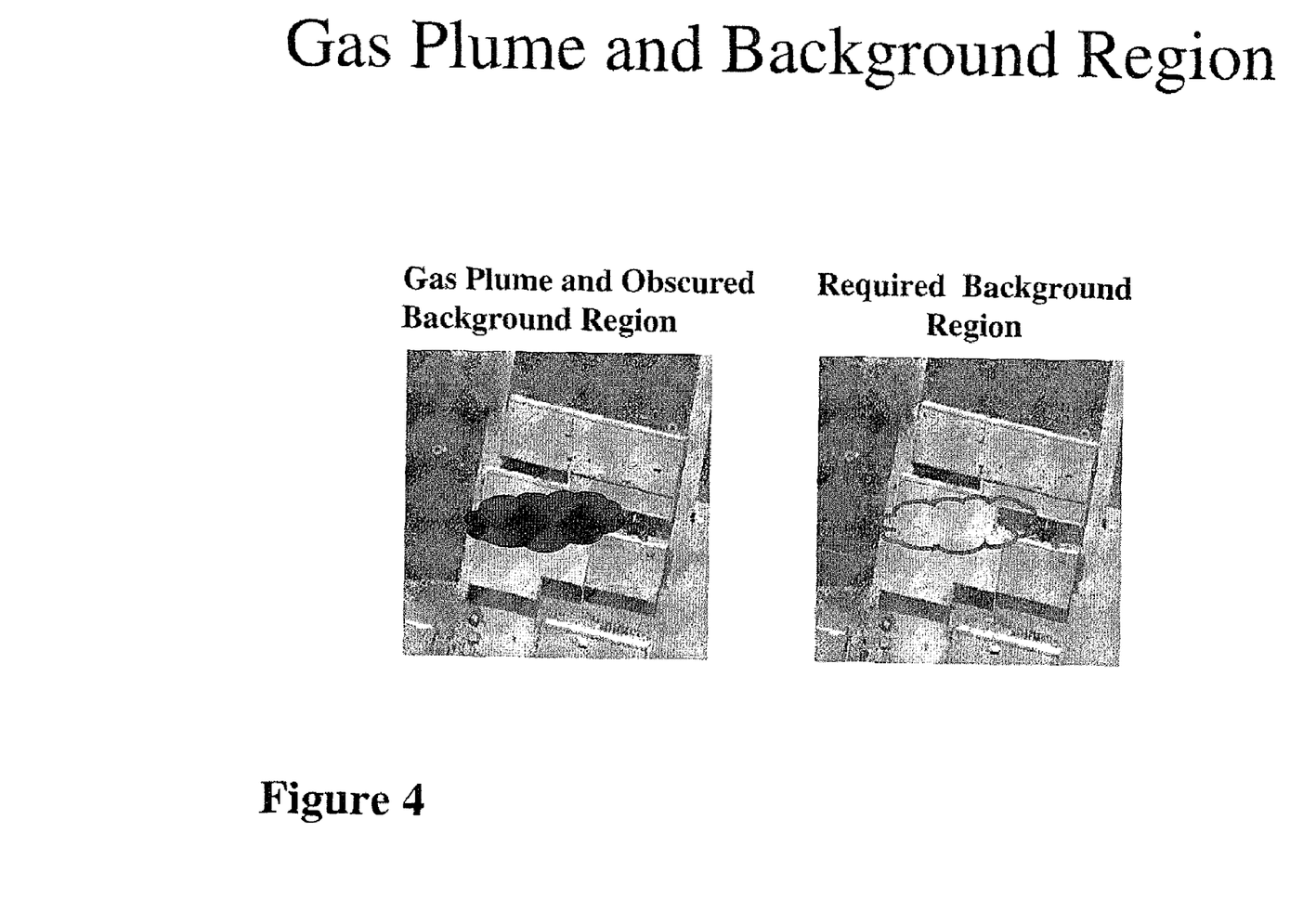
FIG. 4 is an aerial view of a gas plume and its associated background region

It is known that spectral signatures may be used to identify component constituents in gaseous bodies. It is also known that illuminations passing through a gas plume after being reflected or radiated from a background surface exhibit spectral imprints from both the surface and the plume, thereby blurring the distinct radiometric phenomena emanating solely from the gas plume. This complication exists in both passive and active spectral analysis methods as illustrated in FIGS. 1 through 3 at different wavelength-domains of the electromagnetic spectrum. Spectral and radiance data that has been estimated to emanate exclusively from the background may be used to evaluate correctly the gas plume spectral and radiance features. However, the un-obscured view of the background required to capture its data is frequently unavailable as illustrated in FIG. 4. The lack of a reliable method to obtain the data emanating exclusively from the background reduces the ability to properly identify and to accurately quantify the target gases. Therefore, there is a need for a method to obtain the required background spectral and radiance data in order to properly identify and quantity target species in a plume.

SUMMARY OF THE INVENTION

The present invention is a method for remote sensing of the content of a gas plume based on data collected by a satellite, an aerial, or a ground-based imaging sensor, wherein spectral and radiance effects emanating from behind the gas plume are eliminated, or at least reduced.

According to the teachings of the present invention there is provided a method for remote sensing of the content of a gas plume based on spectral data, the method comprising the steps of: (a) deriving a first image taken along a first line of observation of said gas plume with its obscured background; (b) deriving a second image taken along a second line of observation providing an un-obscured view of said background; (c) matching said first and said second images to derive a mapping between pixels of said first image and pixels of said second image; and (d) co-processing spectral data from said correlated images to derive information about the content of the gas plume.

According to a further feature of the present invention, the line of observation is significantly non-parallel to a length of said gas plume.

According to a further feature of the present invention, the aerial imaging sensor is operatively coupled with a tracking mechanism to adjust a tilt of said sensor as it advances along said line of travel thereby ensuring a continual image capture of said plume and background.

According to a further feature of the present invention, the matching said first and second images is implemented by generating a transformed version of one of the images.

According to a further feature of the present invention, the co-processing spectral data from said matched images is implemented by deriving pixel transmittance values and comparing them to known spectral signatures thereby obtaining a best match.

BRIEF DESCRIPTION OF THE DRAWINGS

The invention is herein described, by way of example only, with reference to the accompanying drawings, wherein.

DESCRIPTION OF THE PREFERRED EMBODIMENTS

The principles and operation of the method according to the present invention may be better understood with reference to the drawings and the accompanying description.

Figure 5:
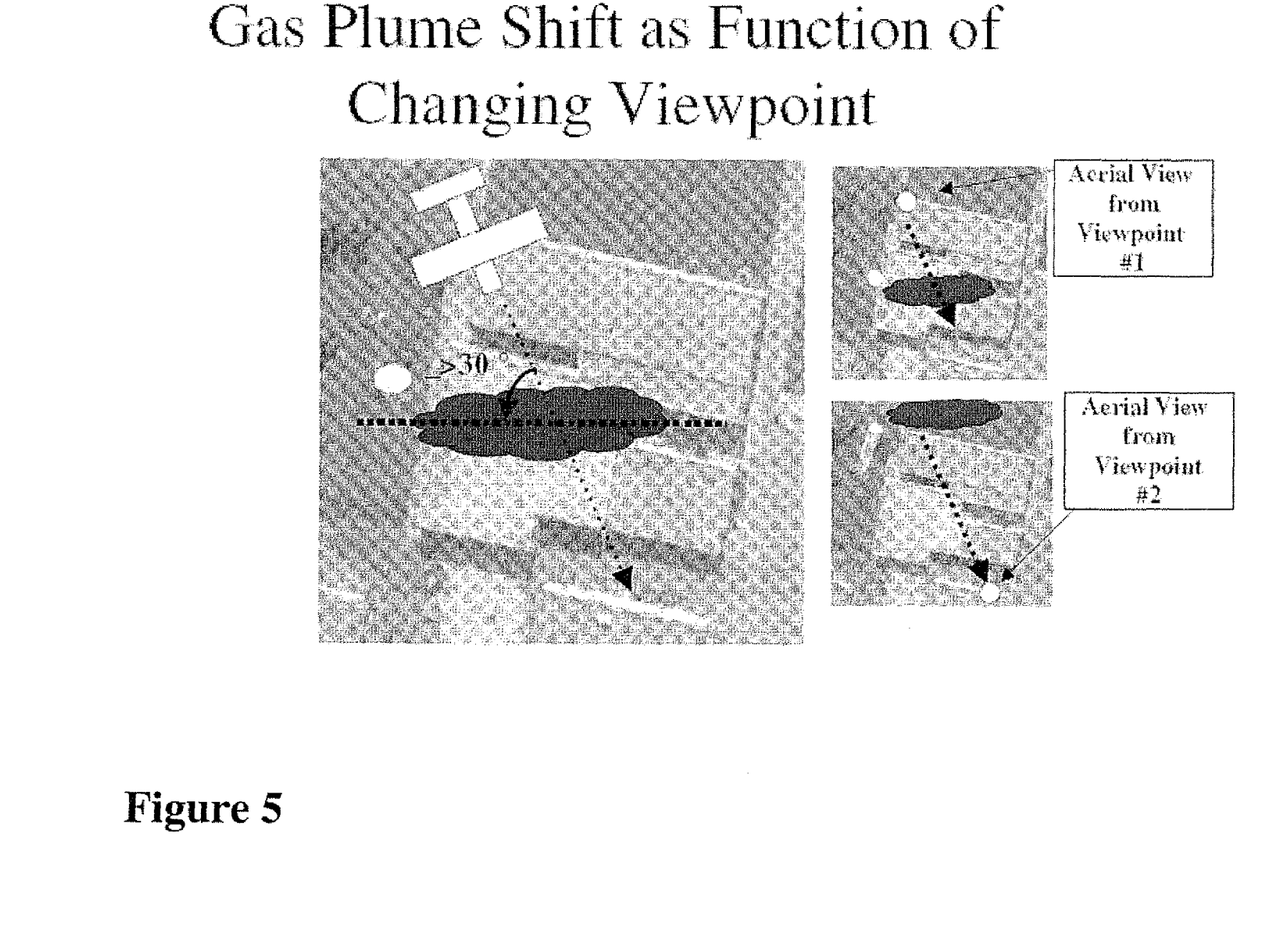
FIG. 5 is an aerial view of gas plume shift as a function of changing viewpoint.
Figure 6:
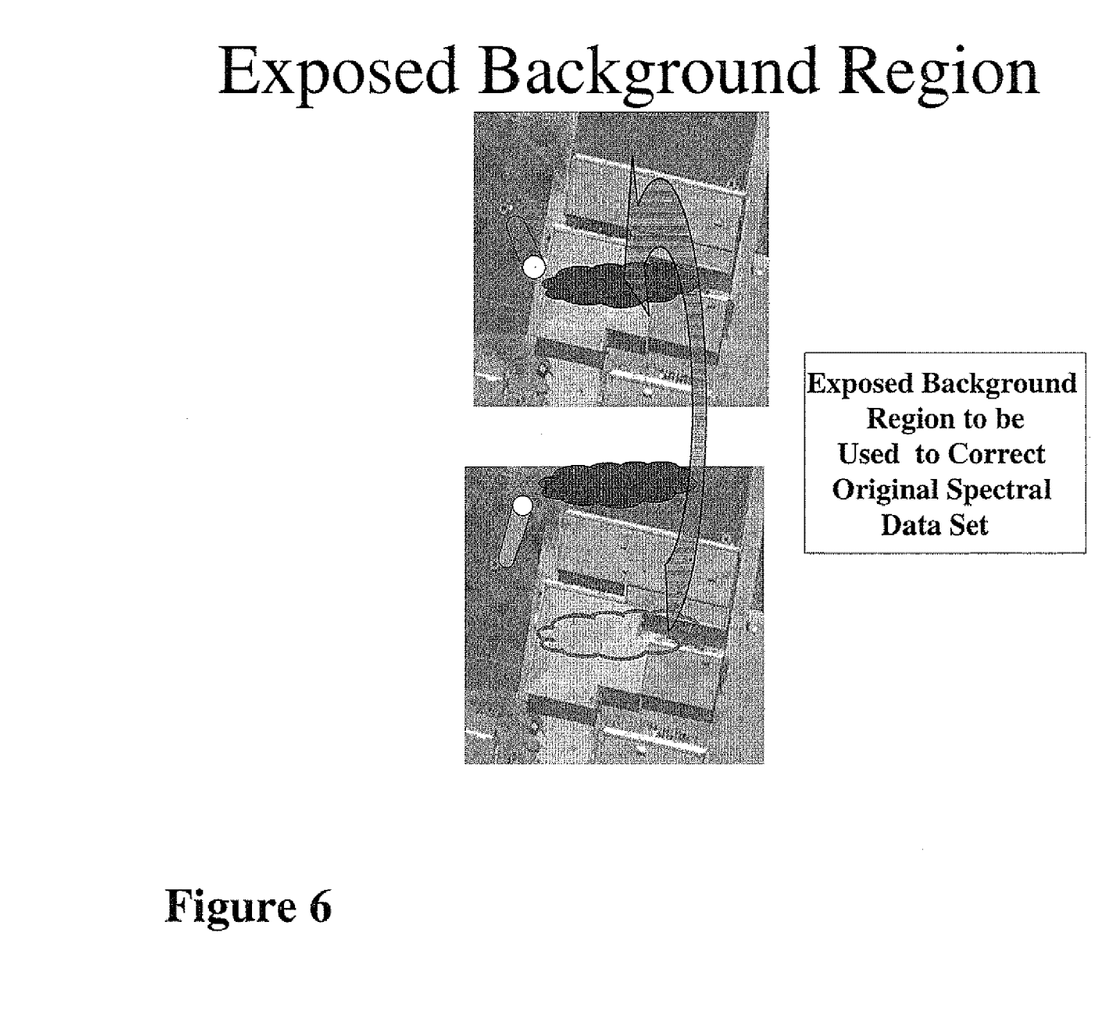
FIG. 6 depicts an exposed background region to be used to correct the original spectral data set.

The present invention, as mentioned above, is a method for remote sensing of the content of a gas plume based on data collected by a satellite, an aerial, or a ground-based imaging sensor, wherein spectral and radiance effects emanating from behind the gas plume are eliminated, or at least reduced. The invention is applicable, but not limited, to monitoring and identifying industrial pollutants, potential public hazards like natural gas leaks, and any other civilian and military applications in which gas plumes are usually released into the atmosphere from a height of at least five meters from the ground. In situations where the prevailing conditions permit, the current invention has application even when the plume is released from lower heights By way of overview, the current invention utilizes the parallax shift phenomena in order to obtain a distinct image of the plume background without the gas plume itself, as shown in FIGS. 4 through 6. It should be noted that each of the depicted embodiments apply to active and passive forms of spectral analysis.

In a non-limiting preferred aerial sensor platform arrangement, a line of flight is chosen so that it is significantly non-parallel to the longitudinal axis of the plume formed by the prevailing wind to ensure the new lines of observation afford unobstructed views of the background region. A typical but non-limiting significant non-parallel line of flight is one that forms an angle relative to the longitudinal axis of the plume exceeding thirty degrees as shown FIG. 4. By way of example, the aerial platform captures images as it advances along a line of travel thereby capturing the images along multiple lines of observation and stores the image data as shown in the flow chart appearing in FIG. 8 designations 61 and 62. An optional, first non-limiting aerial imaging sensor arrangement provides a provision for adjusting the sensor tilt automatically as the aerial platform advances along its line of travel. Preferably the sensor tilt is adjusted by a tracking mechanism configured to direct the sensor at a chosen field of capture as the sensor approaches, passes over, and moves away from the plume. Such an implementation ensures the region of interest falls within the sensor field of capture and is imaged along useful lines of observation providing views of the plume-background combination and the background alone, as shown in FIG. 9.

Figure 10:
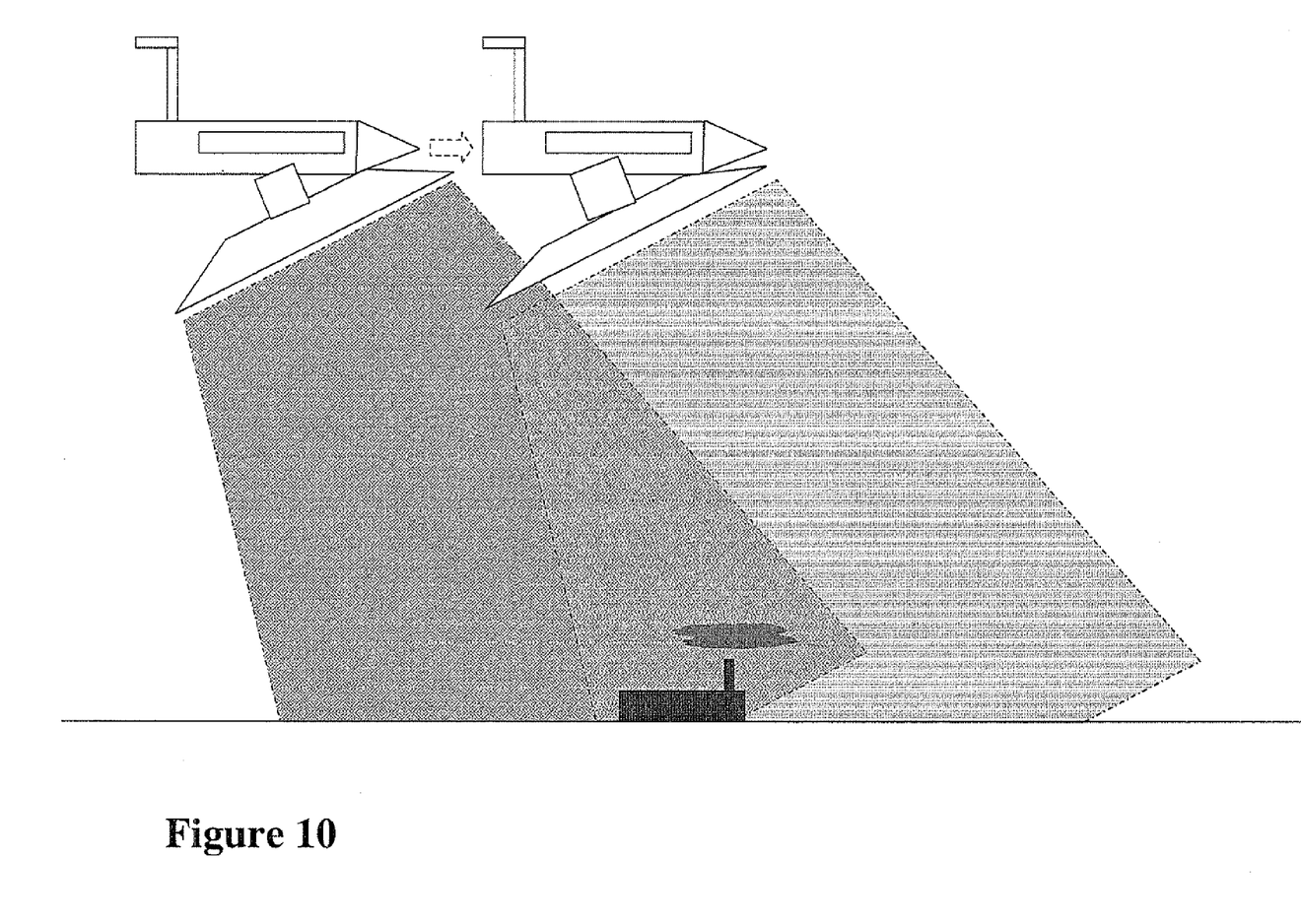
FIG. 10 is a schematic diagram illustrating the fields of image capture for a rigidly mounted image sensor embodiment.

A second optional, aerial imaging sensor arrangement is implemented with a rigidly mounted sensor with a wide capture angle to ensure the visual access along the above-mentioned useful lines of observation providing views of the plume-background combination and the background alone, as shown in FIG. 10.

A second non-limiting sensor platform arrangement is implemented via a satellite orbiting the earth. In a generously analogous manner, the image sensor retrieves the images along changing lines of observation as it advances along its orbit.

A third non-limiting sensor platform arrangement shown in FIG. 3 depicts a ground-based passive sensing scheme in which image sensors are placed in at least two different locations such that each sensor location provides a different line of observation of the plume. Along the first line of observation the first sensor captures an image of the plume against a land surface background whereas along the second line of observation the second sensor captures an image of the land surface background alone. Alternatively, a second ground-based image sensor platform arrangement is implemented as an imaging sensor mounted on vehicle traveling along a route located above the plume so that the sensor captures the needed images along different line of observation as it advances along its line of travel.

It should be noted, the term "aerial platform" is used to refer to any body moving through the atmosphere capable of supporting an imaging device and the term "satellite-mounted platform" refers to any device capable of supporting an imaging device as it orbits the earth.

Figure 8:
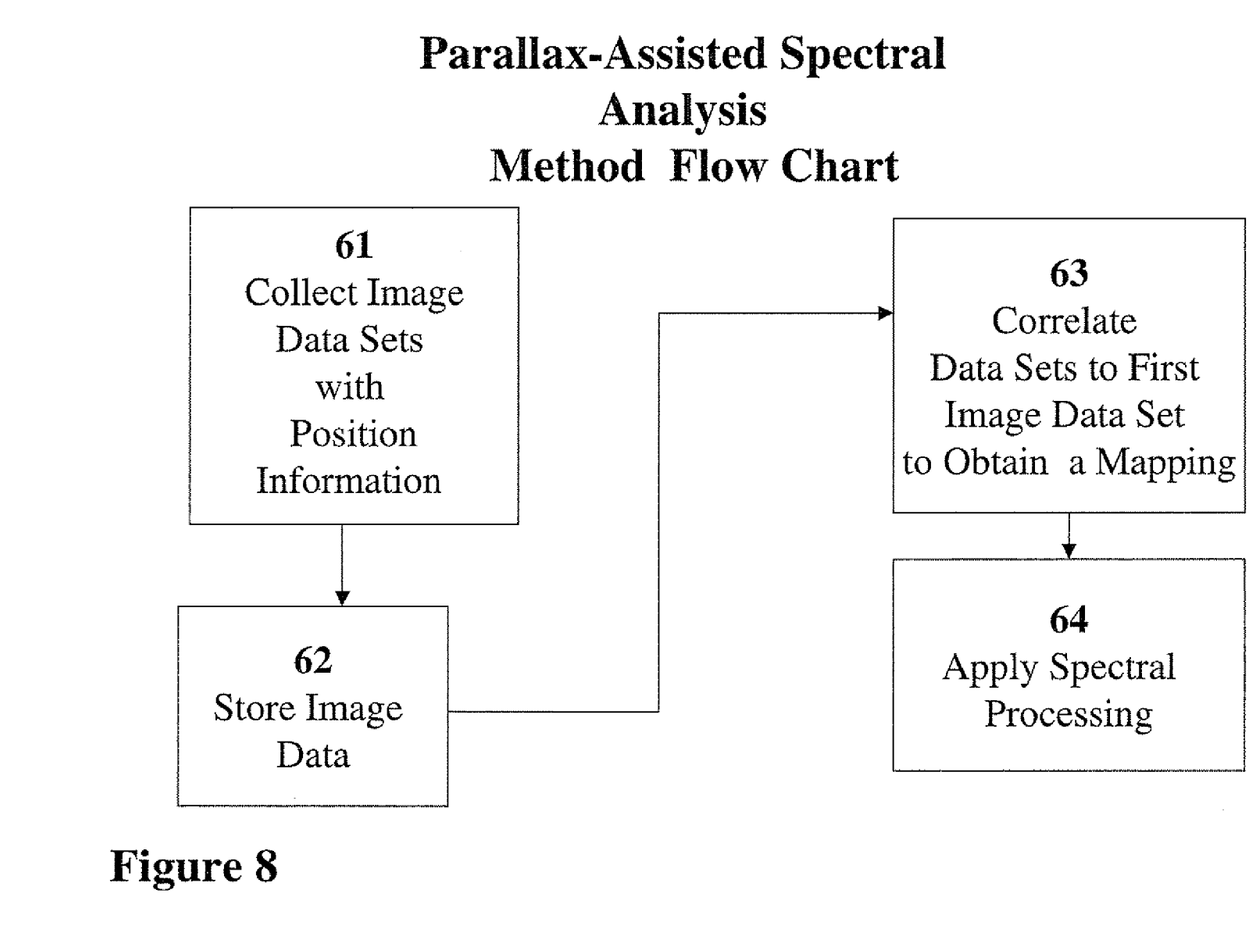
FIG. 8 is a flow chart of a parallax-assisted background correction method for spectral analysis.
Figure 9:
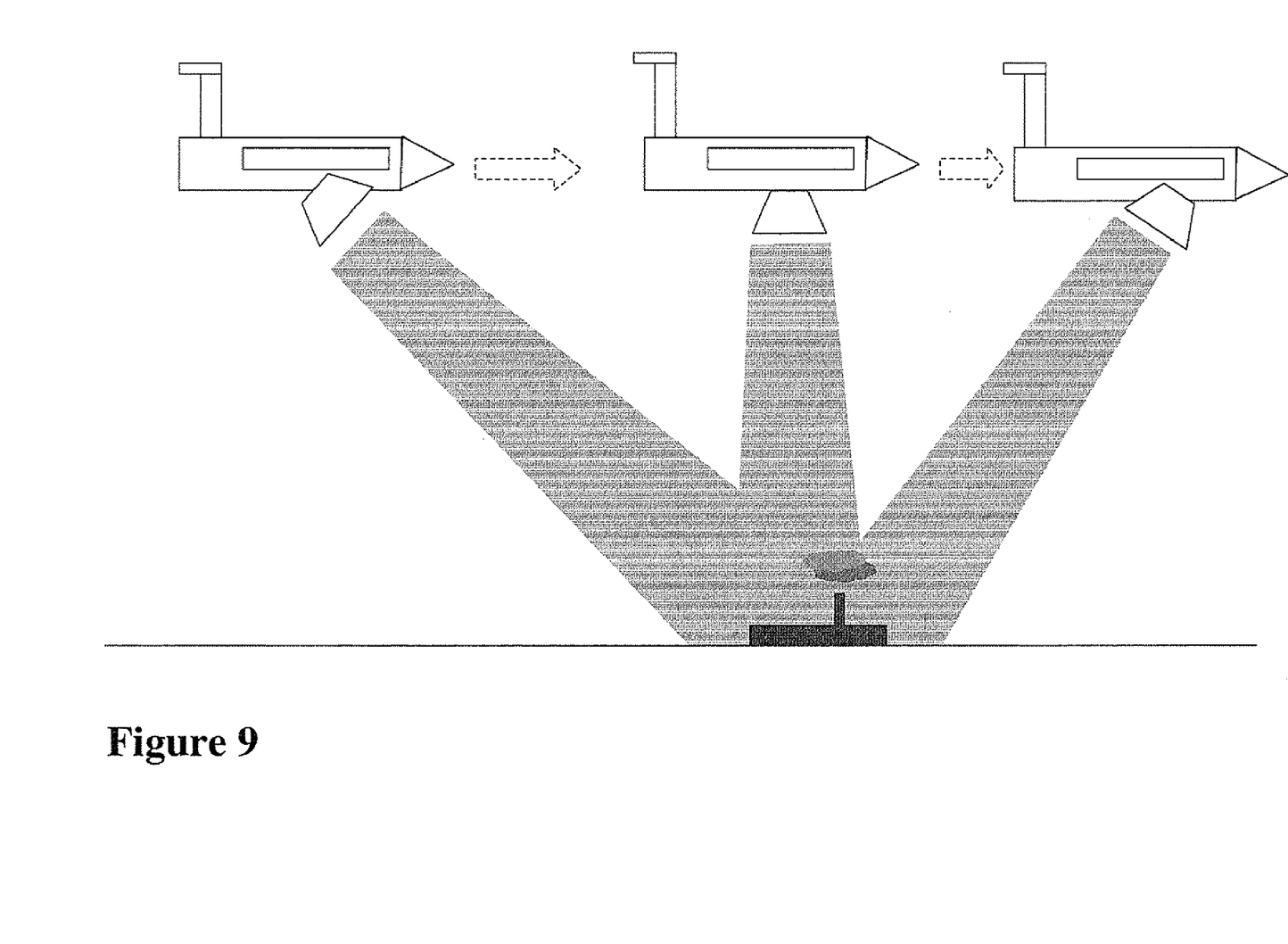
FIG. 9 is a schematic diagram illustrating the fields of image capture for an adjustable tilt image sensor embodiment.

Turning now to the image processing appearing at 63 in FIG. 8, by way of example, the multiple images are matched or registered using known image processing algorithms that derive a pixel-to-pixel mapping for substantially all regions of overlap between the images. In cases where the parallax between the images is small and the background relatively flat, it may be possible to model the mapping by a global parametric transformation. However, in general, the present invention preferably uses stereoscopic processing techniques that identify height/range differences between the different features and provide individual mappings on a feature-by-feature or region-by-region basis within the images. The result is a pixel-to-pixel mapping between the images that enables subsequent spectrum-radiance algorithms and processing of corresponding pixels as if the two images were an image pair taken from exactly the same viewing direction. Optionally, although not necessarily, the mapping can be used to generate a transformed version of one of the images so that the images can be subsequently processed as a normal image pair with directly corresponding pixels. Alternatively, the mapping can be used on-the-fly during subsequent processing to pick out the corresponding pixel pairs. Either way, image-processing 63 renders it possible to perform subsequent pixel-to-pixel comparative spectral processing between the sampled images wherein each image contains the gas plume and a direct view of the region of the background which lies behind the gas plume in the other image.

Once the pixel-to-pixel matching has been established, spectral or other processing is performed to derive information about the content of the gas plume. For example: Looking at each pair of corresponding pixels from two different images, the pixels should be related as images of the same pixel of the background where one is viewed directly and the other is viewed through the gas plume. Spectral processing thus operates by identifying and analyzing, for example, the spectral absorption related to the corresponding pixels which is attributable to the presence of a gas plume, and hence deriving information regarding the position, composition and/or concentration of the gas plume.

The aforementioned processing may be performed by a range of techniques familiar to one ordinarily skilled in the field of spectral analysis. By way of illustration, one non-limiting example of a possible sequence of processing will now be presented in outline. Further details of each step, as well as a variety of variants and alternatives, will be clear to one ordinarily skilled in the art.

Firstly, data must be available (or generated) as to the response of the imaging system in each of the wavelengths measured. It is preferably also determined what gases may be present which would affect the spectral data at the wavelengths measured, and their spectral signatures, at least at the wavelengths measured, are retrieved from a library. In principle, free detection without prior information as to the types of gases sought could be implemented using hyperspectral imaging and processing techniques. However, implementations using a relatively small number of wavelengths (e.g., 2-5 wavelengths) are typically may be only feasible where à priori information is available as to the gas or gases likely to be present.

Preferably, the spectral signatures of the gas or gases are modified to correspond as closely as possible to the viewing conditions under which the images were sampled. Relevant viewing conditions include atmospheric temperature and other atmospheric conditions, and distance to the gas. An adjusted spectral signature taking such factors into consideration may be generated by standard simulator software such as, for example, MODTRAN that is described, for example, in U.S. Pat. No. 5,884,226, and is commercially available from Ontar Corp. (MA, USA). Most preferably, the simulation software is used to generate a working library for different concentrations of the gas, thereby facilitating quantitative analysis of the image data.

Actual processing of the image data then proceeds according to this example by dividing each pixel spectrum from one image by the spectrum of the corresponding pixel of the other image, giving a transmittance spectrum for each pixel. For any given wavelength, a transmittance value of less than 1 indicates absorption at that wavelength while a value greater than 1 indicates emission or reflection from the gas plume. Pixels where no gas is detected in either image should return a flat transmittance spectrum of approximately 1, within limits of the noise level. Similarly, gas that is transparent at that particular wavelength also returns a flat transmittance of approximately 1.

Matching techniques are then applied for each gas in the library, and for each concentration of each gas, to identify a best match gas or combination of gases that correspond to the obtained transmittance spectrum for each pixel, and to derive quantitative information regarding the gas concentration. This processing can be performed by well-known techniques such as the Spectral Angle Mapper (SAM) classification.

It will be noted that division of the spectral data in the "wrong" direction, i.e., dividing the directly viewed background by the data from the gas plume, would result in an inverted transmittance spectrum with absorption appearing as emission and vice versa. Where the number of expected gases is small and/or a large number of wavelengths are sampled, such erroneous data is typically automatically eliminated as a non-fit to any of the expected gases. Optionally, this situation can be avoided altogether by performing initial segmentation of the images on the basis of a priori assumptions as to where the gas plume is expected to appear.

Figure 7:
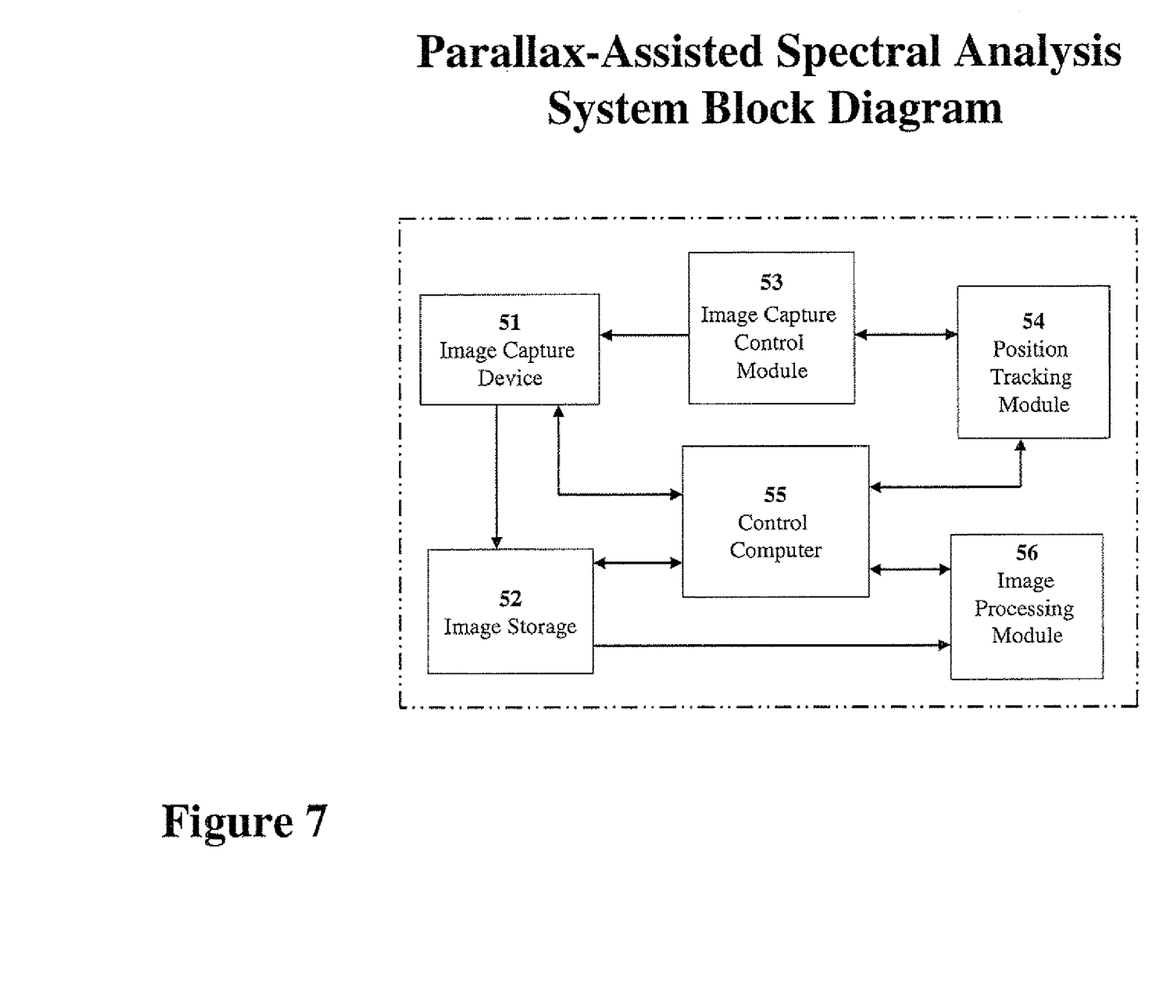
FIG. 7 is a block diagram of a parallax-based correction system for spectral analysis.

The system components for implementing the above processing are shown schematically in FIG. 7. The system as shown includes a Multi-Spectral Image Capture Device 51 for capturing the raw data needed to derive a spectral data set, an Image Storage Module 52 for storing the raw data until processing, an optional Image Capture Control Module 53 and Position Tracking Module 54 for ensuring data capture occurs at appropriate times, an Image Processing Module 56 for processing the data and a Control Computer 55 controlling the system elements and coordinating their interaction.

The Image Capture Control Module 53, based on position information provided by the Position Tracking Module 54, ensures the Image Capture Device 51 captures the appropriate images as it advances along its line of flight.

The Image Capture Control Module 53 also assigns position and height coordinates to each image capture to be used during future processing. Control Computer 55 causes the image data and its associated coordinates to be stored in the Image Storage Module 52. The Image Processing Module 56, under the control of the Control Computer 55, extracts the image data from the Image Storage Module 52 to correlate and to map the image data. With the exception of the Image Capture Device 51, the system components may be located either in a remote platform or at a ground station that communicates with the Image Capture Device 51. As mentioned above, the Image Capture Device 51 may be deployed via an aerial, a satellite or a ground-based platform as illustrated in FIGS. 1 through 3. In a preferred embodiment, the Image Processing Module 56 and the Position Tracking Module 54 are software applications whereas the remaining components are embodied as hardware or as software configured hardware.

It should be noted that the term "multi-spectral" here within refers to imaging on any plurality of wavelengths or bands of wavelengths. The wavelengths may be any wavelengths of visible or invisible light. As thus defined, a conventional color (e.g., RGB) imaging sensor falls within the general term "multi-spectral" In many cases, the invention is applied to image capture devices and processing systems that employ at least two different wavelengths and in some cases specifically employs four different wavelengths. Regarding further matters of terminology for the purposes of the description and claims, unless otherwise specified, systems employing many wavelengths (commonly known as "hyper-spectral" systems) are included within the scope of the generic term "multi-spectral". The term "sensing" refers to the process of detecting and quantifying a gas or gases. The term "obscured" refers to a condition of diminished visibility. For the purpose of this document the condition of being obscured is a function on the viewing wavelength. By way of example, a plume appearing transparent when viewed with visible light but reduces the visibility of its background when viewed at another wavelength has obscured the background at that viewing wavelength. The term "direct view" is used to refer to a view of a region of background in which the light has not passed through the gas plume.

The overall process for reducing the effects of background radiation is may be seen in FIG. 8. The system captures an image of the gas plume with its obscured background region along a first line of observation and continues to capture additional images as it advances along its line of flight. These images are captured at predetermined intervals until the plume and its background are out of range of the Image Capture Device 61. Each image together with its corresponding location data is stored 62.

It will be appreciated that the above descriptions are intended only to serve as examples, and that many other embodiments are possible within the scope of the present invention as defined in the appended claims.

What is claimed is:

1. A method for remote sensing of the content of a gas plume based on spectral data, the method comprising the steps of:
    (a) deriving a first image taken along a first line of observation of said gas plume with its obscured background,
    (b) deriving a second image taken along a second line of observation providing an un-obscured view of said background,
    (c) matching said first and said second images to derive a mapping between pixels of said first image and pixels of said second image, and
    (d) co-processing spectral data from said correlated images to derive information about the content of the gas plume.

2. The method of claim 1, wherein said line of observation is significantly non-parallel to a length of said gas plume.

3. The method of claim 1, wherein said aerial imaging sensor is operatively coupled with a tracking mechanism to adjust a tilt of said sensor as it advances along said line of travel thereby ensuring a continual image capture of said plume and background.

4. The method of claim 1, wherein said matching said first and second images is implemented by generating a transformed version of one of the images.

5. The method of claim 1, wherein said co-processing spectral data from said matched images is implemented by deriving pixel transmittance values and comparing them to known spectral signatures thereby obtaining a best match.

* * * * *